Figure 1:
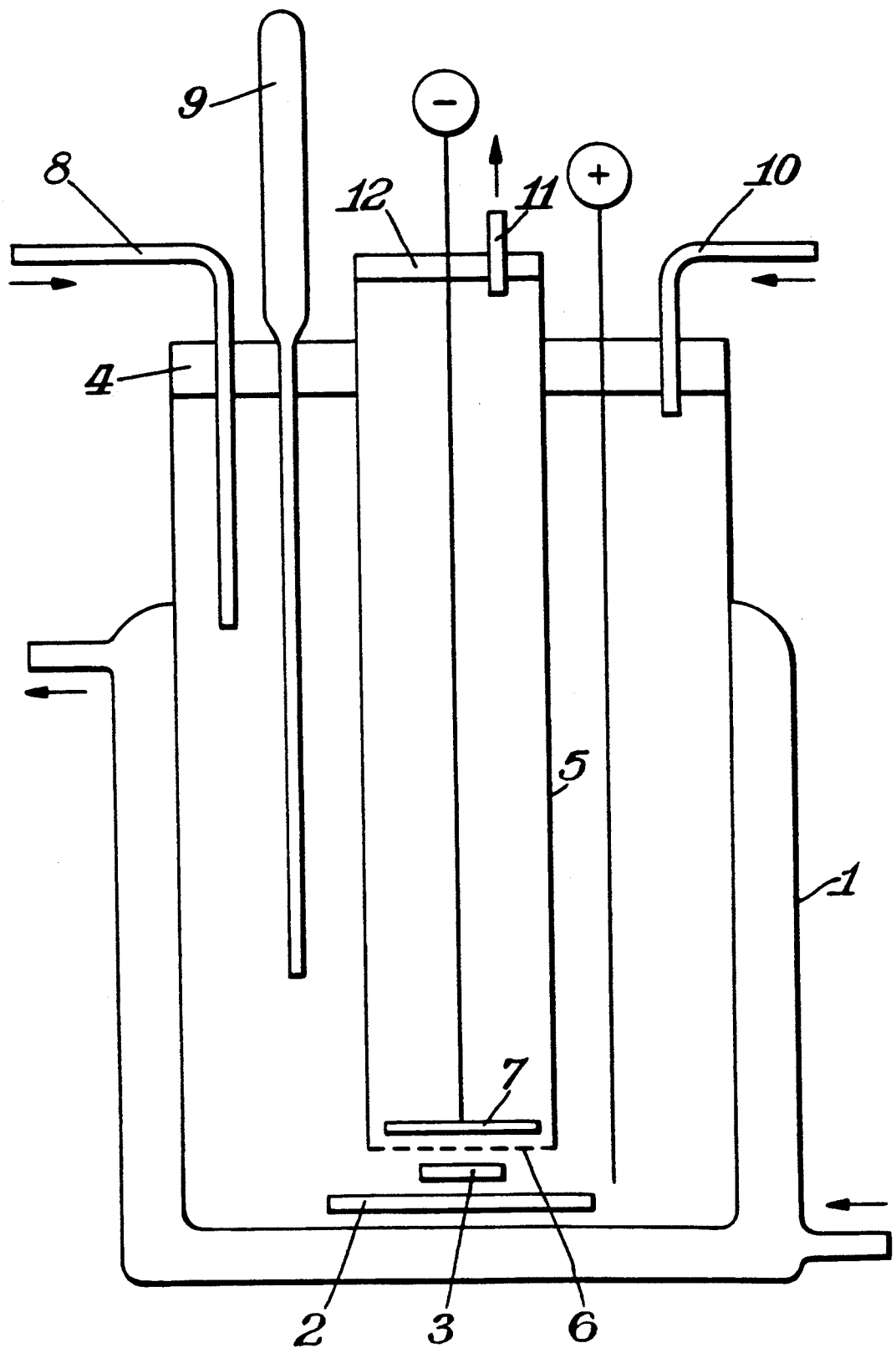

United States Patent [19]

Millauer

[11] Patent Number: 5,328,571
[45] Date of Patent: Jul. 12, 1994

[54] PROCESS FOR PREPARING PERFLUORINATED BROMOALKANES, OR PERFLUORINATED BROMOALKANES CONTAINING ETHER GROUPS

[75] Inventor: Hans Millauer, Eschborn, Fed. Rep. of Germany

[73] Assignee: Hoechst Aktiengesellschaft, Gebäude, Fed. Rep. of Germany

[21] Appl. No.: 119,332

[22] Filed: Sep. 9, 1993

[30] Foreign Application Priority Data

Sep. 23, 1992 [DE] Fed. Rep. of Germany ....... 4231744

[51] Int. Cl.$^5$ .............................................. C25B 3/08
[52] U.S. Cl. .................................. 204/81; 204/59 R; 204/59 F; 204/72
[58] Field of Search ............. 204/59 R, 59 F, 72, 204/81, 267, 295; 570/142; 568/683

[56] References Cited

FOREIGN PATENT DOCUMENTS 1155104 10/1963 Fed. Rep. of Germany .
0949877 2/1964 United Kingdom .

*Primary Examiner*—John Niebling
*Assistant Examiner*—Edna Wong
*Attorney, Agent, or Firm*—Connolly & Hutz

[57] ABSTRACT

Perfluorinated bromoalkanes of the formula $$X-(CF_2)_p-Br \qquad (I),$$

in which X is hydrogen or fluorine and p is an integer from 2 to 10, or perfluorinated bromoalkanes which contain ether groups, of the formula $$CF_3-CF_2-CF_2-O-(CF(CF_3)-CF_2-O)_q-CF(CF_3)-Br, \qquad (Ia)$$

in which q is zero or an integer from 1 to 4, are obtained by electrolytic decarboxylation of a perfluorinated alkanecarboxylic acid of the formula $$X-(CF_2)_p-COOH \qquad (II),$$

in which X is hydrogen or fluorine and p is an integer from 2 to 10, or an alkanecarboxylic acid which contains ether groups, of the formula $$CF_3-CF_2-CF_2-O-(CF(CF_3)-CF_2-O)_q-CF(CF_3)-COOH, \qquad (IIa)$$

in which q is zero or an integer from 1 to 4. The electrolytic decarboxylation is carried out in an aqueous electrolyte in the presence of bromine and an aliphatic nitrile.

15 Claims, 2 Drawing Sheets

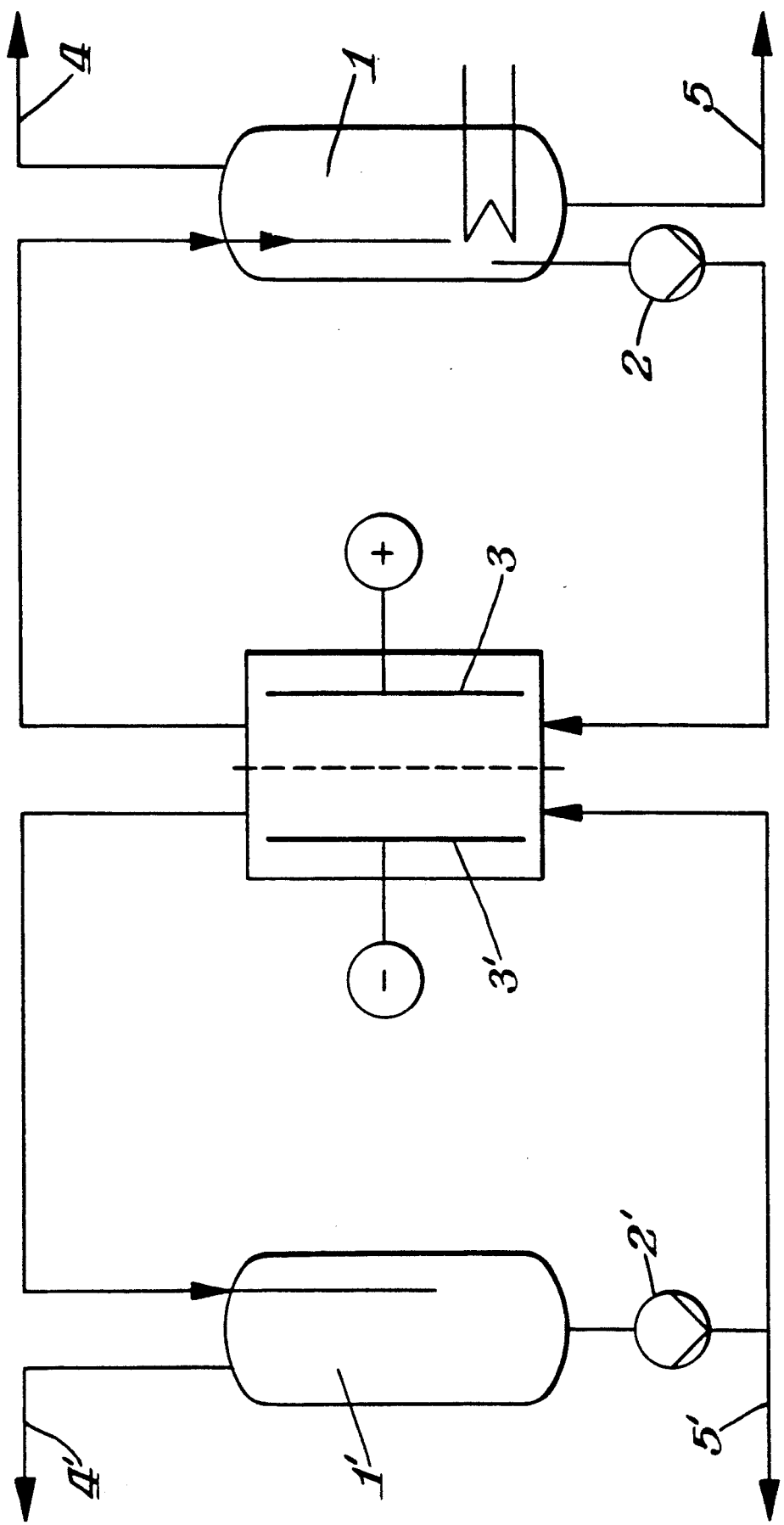

PROCESS FOR PREPARING PERFLUORINATED BROMOALKANES, OR PERFLUORINATED BROMOALKANES CONTAINING ETHER GROUPS

The invention relates to a process for preparing perfluorinated bromoalkanes of the formula $$X-(CF_2)_p-Br \qquad (I)$$

in which X is hydrogen or fluorine and p is an integer from 2 to 10, or perfluorinated bromoalkanes which contain ether groups, of the formula $$CF_3-CF_2-CF_2-O-(CF-CF_2-O)_q CF-Br, \qquad (Ia)$$
$$\qquad\qquad\qquad\quad | \qquad\qquad\quad |$$
$$\qquad\qquad\qquad\; CF_3 \qquad\qquad\; CF_3$$

in which q is zero or an integer from 1 to 4.

Long-chained perfluorinated bromoalkanes such as, for example, perfluoro-1-bromooctane, or perfluorinated bromoalkanes containing ether groups, such as, for example, perfluoro-2-bromo-5-methyl-3,6-dioxanonane, have considerable dissolving power for oxygen and carbon dioxide and are therefore used in the medical sector as a blood substitute and as radiopaque media.

Short-chained perfluorinated bromoalkanes which contain 1 hydrogen atom, such as, for example, H-CF$_2$-CF$_2$-Br are suitable as fire-extinguishing substances having a low ozone-depletion potential.

Perfluorinated bromoalkanes, or perfluorinated bromoalkanes containing ether groups, can be prepared according to various processes:

According to the procedure of DE-C-1 155 104 (GB-PS 949,877) trifluorobromomethane is prepared by bromination of trifluoromethane in the gas state.

According to the procedure of EP-A-0 295 582, perfluorinated bromoalkanes are prepared by decarboxylation of dry salts of perfluorinated alkanecarboxylic acids or oxaalkanecarboxylic acids in the presence of bromine in an aprotic solvent.

The object of the invention is therefore to provide a process for preparing perfluorinated bromoalkanes, and perfluorinated bromoalkanes containing ether groups, in which process fluoroalkanecarboxylic acids, and fluoroalkanecarboxylic acids containing ether groups, are reacted as the starting materials. The starting materials are to be converted into the desired end product with a high yield and good purity. It is also to be possible for the process to be operated continuously.

Surprisingly, the object could be achieved by subjecting a perfluorinated alkanecarboxylic acid of the formula $$X-(CF_2)_p-COOH \qquad (II),$$

in which X is hydrogen or fluorine and p is an integer from 2 to 10, or an alkanecarboxylic acid which contains ether groups, of the formula $$CF_3-CF_2-CF_2-O-(CF-CF_2-O)_q CF-COOH, \qquad (IIa)$$
$$\qquad\qquad\qquad\quad | \qquad\qquad\quad |$$
$$\qquad\qquad\qquad\; CF_3 \qquad\qquad\; CF_3$$

in which q is zero or an integer from 1 to 4, to electrolytic decarboxylation in an aqueous electrolyte in the presence of bromine and an aliphatic nitrile.

The process according to the invention may optionally and preferably be distinguished in that
a) an aliphatic nitrile having from 1 to 6 carbon atoms is used;
b) the aliphatic nitrile used is acetonitrile, propionitrile or isobutyronitrile;
c) the aqueous electrolyte electrolyzed is a mixture comprising
from 1 to 40% by weight of nitrile
from 1 to 70% by weight of alkanecarboxylic acid of the formula II or IIa
from 5 to 100 mol % of alkali metal hydroxide, based on the alkanecarboxylic acid
from 50 to 200 mol % of bromine, based on the alkanecarboxylic acid
the remainder being water;
d) the alkanecarboxylic acids used are
α) omega-H-perfluoroalkanoic acids of the formula II with X=H: 3-H-perfluoropropionic acid, 5-H-perfluoropentanoic acid, 7-H-perfluoroheptanoic acid, 9-H-perfluorononanoic acid;
β) perfluoroalkanoic acids of the formula II with X=F: perfluoropentanoic acid, perfluorohexanoic acid, perfluoroheptanoic acid, perfluorooctanoic acid, perfluorononanoic acid, perfluorodecanoic acid or perfluoroundecanoic acid;
γ) perfluoroethercarboxylic acids of the formula IIa: perfluoro-2-methyl-3-oxahexanoic acid, perfluoro-2,5-dimethyl-3,6-dioxanonanoic acid, perfluoro-2,5,8-trimethyl-3,6,9-trioxadodecanoic acid or perfluoro-2,5,8,11-tetramethyl-3,6,9,12-tetraoxapentadecanoic, acid;
e) the alkanecarboxylic acids are employed in neutralized or partially neutralized form;
f) the alkali metal hydroxide employed for neutralization or part-neutralization of the alkanecarboxylic acid is sodium hydroxide, potassium hydroxide or tetraalkylammonium hydroxide;
g) during the electrolytic decarboxylation more alkanecarboxylic acid in non-neutralized form is metered in to the extent in which it is consumed in the electrolytic decarboxylation;
h) the bromine is added to the electrolyte in portions or continuously during the electrolytic decarboxylation;
i) a current density of 20 to 500, especially from 50 to 250, mA/cm$^2$ is set;
j) the electrolytic decarboxylation is carried out at temperatures between $-10°$ C. and $50°$ C.;
k) the electrolytic decarboxylation is carried out in undivided beaker cells or flow cells;
the electrolytic decarboxylation is carried out in a divided electrolytic cell, the anolyte compartment and cathode compartment being separated from one another by an ion-selective membrane or a diaphragm;
m) the alkanecarboxylic acid and the bromine are placed into the anolyte compartment.

If a divided electrolytic cell is used, the alkanoic acid is expediently employed in neutralized form. If undivided electrolytic cells are used, degrees of neutralization between 5 and 100% are more expedient.

The materials employed for the anode are platinum or other noble metals, metals coated with platinum or other noble metals, and vitreous carbon. The materials used for the cathode are those mentioned as anode materials and graphite or titanium.

Surprisingly, the desired products of the formula I and Ia are formed only if mixtures of water and nitrile are used as the electrolyte. In contrast, no products of the formula I or Ia are obtained if either water only or a nitrile only is employed as the electrolyte.

The invention is explained in more detail with reference to FIGS. 1 and 2 and to the examples:

EXAMPLE 1

In Example 1 a beaker cell, as shown diagrammatically in FIG. 1 in a vertical section, is used. On the bottom of a cylindrical glass vessel, which has an internal diameter of 100 mm and a height of 150 mm and which is provided with an external cooling jacket 1, there is a circular platinum sheet (area approximately 35 $cm^2$) which serves as the anode 2. On the anode there lies a magnetic stirring rod 3 having a length of 30 mm. The cell is closed with a polythene stopper 4 which is provided with a plurality of bores. Through the central bore, a polythene tube 5 (internal diameter 50 mm) is passed which, at its lower end, is sealed by a horizontally positioned cation exchanger membrane 6 (Nafion® 427) clamped by means of a screw cap. The tube 5 at its head is closed by a polythene stopper 12. In the cathode chamber thus formed there is a likewise horizontally positioned chromium-nickel steel netting (area approximately 23 $cm^2$) which serves as the cathode 7. Through the stopper 4, a nitrogen-inlet tube 8 and a thermometer 9 are introduced in addition. Gaseous reaction products escape from the anode chamber and the cathode chamber through the offtakes 10 and 11. The anolyte employed is a neutral solution of 92.8 g (0.20 mol) of perfluorononanoic acid (formula II, X=F, p=8) in 230 g of 0.35% by weight aqueous sodium hydroxide, 100 g of acetonitrile and 24 g (0.30 mol) of bromine. The catholyte comprises 100 g of 1% by weight aqueous sodium hydroxide.

Electrolysis is carried out at a temperature of 20° C. and a current of 1.8 ampere up to a charge throughput of 0.25 Faraday, the stirring rate of the magnetic rod being 600 rpm. After electrolysis, the separated product is removed in the separating funnel, washed with water and dried over sodium sulfate. 97.2 g of crude product are obtained which, according to gas-chromatographic analysis, contains 95.1% of perfluoro-1-bromooctane (formula I, X=F, p=8). The product yield calculated therefrom is 92.5%; the current yield is 80%. Fractional distillation gives a product having a boiling point of 140° to 141° C.

EXAMPLE 2

Example 1 is repeated with a different material used. Starting from 82.8 g (0.20 mol) of perfluorooctanoic acid (formula II, X=F, p=7) and 24 g (0.30 mol) of bromine, 84.2 g of perfluoro-1-bromoheptane (formula I, X=F, p=7) are obtained with a purity of 93%. This corresponds to a product yield of 87.2% and a current yield of 72.5%. Fractional distillation gives a colorless product having a boiling point of 121°-122° C.

EXAMPLE 3

The apparatus described in Example 1 is used for Example 3. The reaction products escaping from offtake 10 are passed through wash bottles connected in series, first into 20% by weight aqueous sodium hydroxide, then into concentrated sulfuric acid and finally through a cold trap cooled with dry ice.

In order to prepare the anolyte, 98 g (0.67 mol) of 3-H-perfluoropropanoic acid (formula II, X=H, p=2) are mixed with a solution of 26.8 g (0.67 mol) of sodium hydroxide in 100 g of water and are then admixed with 20 g of acetonitrile and with 6 g of bromine. The catholyte comprises 25% by weight sulfuric acid.

The electrolysis is carried out with a stirring speed of the magnetic rod of 500 rpm at a temperature of 10° C. and an initial current of 3 ampere. After a charge throughput of 0.67 Faraday, the current is lowered to 2 ampere. The total electric charge is 0.90 Faraday. The cell voltage is between 12 and 14 volt.

As the electrolysis proceeds, a further 60 g of bromine are added to the anolyte in 12 portions. After electrolysis, the anolyte is heated to 40° C, and the remaining product is driven over by means of a gentle nitrogen stream.

The colorless condensate (80.2 g) formed in the cold trap contains, according to gas-chromatographic analysis, 94.7% of 1-bromo-1,1,2,2-tetrafluoroethane (formula I, X=H, p=2) and 4.7% of 1,1,2,2,3,3,4,4-octafluorobutane, 0.3% of acetonitrile and 0.3% of an unknown compound. The product yield calculated therefrom is 63%; the current yield is 46%.

EXAMPLE 4

The apparatus described in Example 1 is used for Example 4.

In order to prepare the anolyte, 123 g (0.50 mol) of 5-H-perfluoropentanoic acid (formula II, X=H, p=4) are mixed with a solution of 28 g (0.50 mol) of potassium hydroxide in 150 g of water and are then admixed with 50 g of acetonitrile and 6 g of bromine. The catholyte comprises 25% by weight sulfuric acid.

The electrolysis is carried out with a stirring speed of the magnetic rod of 500 rpm at a temperature of 10° C. and a current of 2.5 ampere. The electric charge is 0.67 Faraday, The cell voltage is between 12 and 24 volt. As the electrolysis proceeds, a further 50 g of bromine are added to the anolyte in 10 portions.

After electrolysis, the lower phase of the anolyte is separated and successively washed twice with ice cold 1% by weight aqueous sodium hydroxide, with concentrated sulfuric acid and water. The crude product obtained (96 g) consists, according to gas-chromatographic analysis, to 97% of 1-bromo-1,1,2,2,3,3,4,4-octafluorobutane (formula I, X=H, p=4). Distillation gives a product boiling at 66 to 67° C. The product yield is 66%, the current yield is 55%.

EXAMPLE 5

Example 5 is carried out in a configuration having a divided flow cell with plate-shaped electrodes arranged in parallel and each having an electrode area of 200 $cm^2$, as diagrammatically shown in FIG. 2. The anode comprises a platinum sheet. A graphite plate serves as the cathode. The cell is divided by a cation exchanger membrane (Nafion® 427).

The anolyte circuit comprises the anolyte vessel 1 provided with a cooling coil, the anolyte pump 2 and the anode compartment 3 of the electrolytic cell. The anolyte vessel 1 serves to separate the gaseous reaction products which escape via the gas offtake 4. Removal of the liquid reaction products is effected via the offtake line 5. The catholyte circuit is formed by the catholyte vessel 1', the catholyte pump 2' and the cathode compartment 3' of the electrolytic cell. The hydrogen formed during electrolysis escapes through the gas offtake 4'. Via the offtake line 5', the alkali metal hydroxide solution formed cathodically is drawn off. Connected to the gas offtake 4 of the anolyte circuit there is a trap cooled with dry ice.

The anolyte circuit is charged with a solution of 743 g (2.25 mol) of perfluoro-2-methyl-3-oxahexanoic acid (formula IIa, q=0; purity approximately 98%), which is neutralized with 1,600 g of 5.7% by weight aqueous sodium hydroxide to pH 5 and is then admixed with 500 g of acetonitrile and 180 g (2.25 mol) of bromine.

The catholyte circuit is charged with 300 g of 1% by weight aqueous sodium hydroxide. The pumpover rate of the anolyte is 200 l/h, that of the catholyte 50 l/h. The electrolysis is carried out at a temperature of 25°-30° C. and a current of 30 ampere up to a charge throughput of 2.92 Faraday; the cell voltage required in the process increases from an initial 7 volt to approximately 13 volt. In the course of the electrolysis, a further 180 g of bromine are added dropwise in a continuous manner. The pH of the anolyte is kept between 3 and 3.5 during the electrolysis by adding 5.7% by weight aqueous sodium hydroxide. The crude product separating from the anolyte as the higher-density phase and the product collected in the cold trap are together washed with 5% by weight aqueous sodium hydroxide. 692 g of crude product are obtained which has the following composition, determined by gas chromatography (data in area %):

97.8% perfluoro-2-bromo-3-oxahexane (formula Ia; q=0)
1.3% dimer product
0.6% perfluoro-2-bromo-5-methyl-3,6-dioxanonane (formula Ia; q=1)

From this, a product yield of 82.4% is calculated, based on the acid employed, and a current yield of 63.3%.

EXAMPLE 6

The apparatus described in Example 5 is used for Example 6.

The anolyte circuit contains 992 g (2.00 mol) of perfluoro-2, 5-dimethyl-3,6-dioxanonanoic acid (formula IIa, q=1) which has been neutralized to pH 5-6 with 1,200 g of 6.7% by weight aqueous sodium hydroxide, 500 g of acetonitrile and 120 g (1.50 mol) of bromine. The catholyte circulation comprises 300 g of 1% by weight aqueous sodium hydroxide.' The pumpover rate of the anolyte is 200 l/h, that of the catholyte 50 l/h. At a current of 30 ampere and a temperature of 30° C., electrolysis is carried out up to a charge throughput of 2.4 Faraday at a cell voltage of 7.5-12.5 volt. In the course of the first half of the electrolysis, a further 120 g of bromine are continuously metered into the anolyte. During the electrolysis, the pH of the anolyte is kept between 3 and 4 by adding 6.7% by weight aqueous sodium hydroxide. The product is drawn off as the higher-density phase from the anolyte via the offtake line 5. After washing with 5% by weight aqueous sodium hydroxide, 974 g of crude product are obtained which has the following composition, determined by gas chromatography (data in area %):

97.1% perfluoro-2-bromo-5-methyl-3,6-dioxanonane (formula Ia, q=1)
2.6% dimer product
0.3% perfluoro-2-bromo-3-oxahexane (formula Ia, q=0)

From this, a product yield of 89% is calculated, based on the acid employed, and a current yield of 74%°

EXAMPLE 7

The apparatus described in Example 5 is used for Example 7.

The anolyte circuit is charged with a solution which was prepared in the following way: 1,324 g (2.0 mol) of perfluoro-2, 5,8-trimethyl-3,6,9-trioxadodecanoic acid (formula IIa, q=2) are mixed with 1,200 g of 6.7% by weight aqueous sodium hydroxide and admixed with 500 g acetonitrile and 120 g (1.5 mol) of bromine. The catholyte circulation comprises 300 g of 1% by weight aqueous sodium hydroxide. The pumpover rate of the anolyte is 200 l/h, that of the catholyte 50 l/h.

At an electrolysis temperature of 25°-30° C. and a current of 20 ampere, electrolysis is carried out up to a charge throughput of 2.4 Faraday at a cell voltage of 7-14 volt. In the course of the electrolysis, a further 160 g of bromine are continuously metered into the anolyte. After termination of the electrolysis, the higher-density phase is separated from the anolyte and washed with 5% by weight aqueous sodium hydroxide. The residue obtained is 1,126 g of crude product which has the following composition, determined by gas chromatography (data in area %):

96.5% perfluoro-2-bromo-5,8-dimethyl-3,6,9-trioxadodecane (formula Ia, q=2)
1.5% dimer product
0.8% perfluoro-2-bromo-5-methyl-3,6-dioxanonane (formula Ia, q=1)

This corresponds to a product yield of 78%, based on the acid employed, and a current yield of 73%.

We claim:

1. A process for preparing perfluorinated bromoalkanes of the formula

$$X-(CF_2)_p-Br \qquad (I),$$

in which X is hydrogen or fluorine and p is an integer from 2 to 10, or perfluorinated bromoalkanes which contain ether groups, of the formula

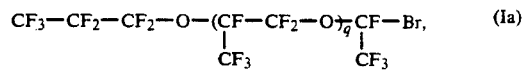

in which q is zero or an integer from 1 to 4, which comprises subjecting a perfluorinated alkanecarboxylic acid of the formula

$$X-(CF_2)_p-COOH \qquad (II),$$

in which X is hydrogen or fluorine and p is an integer from 2 to 10, or an alkanecarboxylic acid which contains ether groups, of the formula

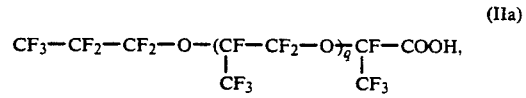

in which q is zero or an integer from ! to 4, to electrolytic decarboxylation in an aqueous electrolyte in the presence of bromine and an aliphatic nitrile.

2. The process as claimed in claim 1, wherein an aliphatic nitrile having from 1 to 6 carbon atoms is used.

3. The process as claimed in claim 1, wherein the aliphatic nitrile used is acetonitrile, propionitrile or isobutyronitrile.

4. The process as claimed in claim 1, wherein the aqueous electrolyte electrolyzed is a mixture comprising from 1 to 40% by weight of nitrile
from 1 to 70% by weight of alkanecarboxylic acid of the formula II or IIa
from 5 to 100 mol % of alkali metal hydroxide, based on the alkanecarboxylic acid
from 50 to 200 mol % of bromine, based on the alkanecarboxylic acid the remainder being water.

5. The process as claimed in claim 1, wherein the alkanecarboxylic acids used are α) omega-H-perfluoroalkanoic acids of the formula II with X=H: 3-H-perfluoropropionic acid, 5-H-perfluoropentanoic acid, 7-H-perfluoroheptanoic acid, 9-H-perfluorononanoic acid;

β) perfluoroalkanoic acids of the formula II with X=F: perfluoropentanoic acid, perfluorohexanoic acid, perfluoroheptanoic acid, perfluorooctanoic acid, perfluorononanoic acid, perfluorodecanoic acid or perfluoroundecanoic acid;

γ) perfluoroethercarboxylic acids of the formula II a: perfluoro-2-methyl-3-oxahexanoic acid, perfluoro-2,5-dimethyl-3,6-dioxanonanoic acid, perfluoro-2,5,8-trimethyl-3,6,9-trioxadodecanoic acid or perfluoro-2,5,8,11-tetramethyl-3,6,9,12-tetraoxapentadecanoic acid.

6. The process as claimed in claim 1, wherein the alkanecarboxylic acids are employed in neutralized or partially neutralized form.

7. The process as claimed in claim 6, wherein the neutralization is by alkali metal hydroxide selected from the group consisting of sodium hydroxide or potassium hydroxide.

8. The process as claimed in claim 1, wherein during the electrolytic decarboxylation more alkanecarboxylic acid in non-neutralized form is metered in to the extent in which it is consumed in the electrolytic decarboxylation.

9. The process as claimed in claim 1, wherein the bromine is added to the electrolyte in portions or continuously during the electrolytic decarboxylation.

10. The process as claimed in claim 1, wherein a current density of 20 to 500 mA/cm$^2$ is set.

11. The process as claimed in claim 1, wherein the electrolytic decarboxylation is carried out at temperatures between $-10°$ C. and $50°$ C.

12. The process as claimed in claim 1, wherein the electrolytic decarboxylation is carried out in undivided beaker cells or flow cells.

13. The process as claimed in claim 1, wherein the electrolytic decarboxylation is carried out in a divided electrolytic cell, the anolyte compartment and cathode compartment being separated from one another by an ion-selective membrane or a diaphragm.

14. The process as claimed in claim 13, wherein the alkanecarboxylic acid and the bromine are placed into the anolyte compartment.

15. The process as claimed in claim 6, wherein the neutralization is by tetraalkylammonium hydroxide.

* * * * *